United States Patent
Wilkins, Jr.

(10) Patent No.: US 7,041,706 B2
(45) Date of Patent: May 9, 2006

(54) METHOD FOR TREATING CROHN'S DISEASE

(76) Inventor: Joe S. Wilkins, Jr., 921 Marine Dr. #102A, Galveston, TX (US) 77550

( * ) Notice: Subject to any disclaimer, the term of this patent is extended or adjusted under 35 U.S.C. 154(b) by 112 days.

(21) Appl. No.: 10/419,572

(22) Filed: Apr. 21, 2003

(65) Prior Publication Data
US 2003/0199592 A1    Oct. 23, 2003

Related U.S. Application Data

(60) Provisional application No. 60/373,905, filed on Apr. 19, 2002.

(51) Int. Cl.
A61K 31/015 (2006.01)
A61K 35/78 (2006.01)

(52) U.S. Cl. .................. 514/764; 424/736
(58) Field of Classification Search ........... 514/764; 424/736
See application file for complete search history.

(56) References Cited

U.S. PATENT DOCUMENTS

| | | |
|---|---|---|
| 3,882,248 A | 5/1975 | Igimi et al. |
| 4,338,251 A | 7/1982 | Sato et al. |
| 4,435,423 A | 3/1984 | Sato et al. |
| 4,468,458 A | 8/1984 | Sato et al. |
| 4,595,694 A | 6/1986 | Takase et al. |
| 4,675,313 A | 6/1987 | Arias |
| 4,888,417 A | 12/1989 | Shiraga et al. |
| 5,153,229 A | 10/1992 | Chastain et al. |
| 5,229,425 A | 7/1993 | Chastain et al. |
| 5,270,344 A | 12/1993 | Herman |
| 5,308,872 A | 5/1994 | Chastain et al. |
| 5,308,873 A | 5/1994 | Chastain et al. |
| 5,543,435 A | 8/1996 | Chastain et al. |
| 5,889,049 A | 3/1999 | Juergens |
| 6,294,586 B1 | 9/2001 | Yelle et al. |
| 6,420,435 B1 | 7/2002 | Wilkins, Jr. |

FOREIGN PATENT DOCUMENTS

| | | | |
|---|---|---|---|
| DK | WO 99/35116 | * | 7/1999 |
| GB | 2135990 A | | 9/1984 |
| JP | 356113718 A | | 9/1981 |
| JP | 361271297 A | | 12/1986 |
| JP | 62174035 A2 | | 7/1987 |
| JP | 1066115 A | | 3/1989 |
| JP | 402142743 A | | 5/1990 |
| JP | 10226640 A | | 8/1998 |

OTHER PUBLICATIONS

U.S. Appl. No. 10/615,589, filed Jul. 2003, Wilkins, Jr.
U.S. Appl. No. 10/615,588, filed Jul. 2003, Wilkins, Jr.
C. Tuffnell, "Hops—A Traditional Herb with New Possibilities," Presentation to Herbal Medicine Seminar a Canterbury College of Natural Medicine, Christchurch, New Zealand (Jul. 2001) (5 pages).
Chemical Abstracts printout—Van Lieshout, E.M., et al., Effects of Dietary Anticarcinogens on Rat Gastrointestinal Glutathione Peroxidase Activity, 5(4) *Oncol. Rep.*, 959-963 (1998).
Chemical Abstracts printout—Rodriguez, A.M., et al., "Structure-Activity Relationship of Limonene Derivatives Acting as Gastric Cytoprotextive Agents," 82(5) *An. Asoc. Quim, Argent.*, 399-414 (1994).
Chemical Abstracts printout—Van Lieshout, E.M., et al., Effects of Dietary Anticarcinogens on Rat Gastrointestinal Glutathione S-Transferase Theta I-1 Levels, 19(11) *Carcinogenesis.* 2055-2057 (1998).

* cited by examiner

Primary Examiner—Christopher S. F. Low
Assistant Examiner—Leslie A. Royds
(74) Attorney, Agent, or Firm—Laura G. Barrow

(57) ABSTRACT

Methods of treating Crohn's Disease comprising orally administering therapeutically effective amounts of limonene are described herein.

6 Claims, No Drawings

METHOD FOR TREATING CROHN'S DISEASE

This application claims the benefit of the filing of co-pending U.S. Provisional application No. 60/373,905, filed Apr. 19, 2002, and which is incorporated by reference herein in its entirety.

BACKGROUND AND SUMMARY OF THE INVENTION:

Crohn's Disease (CD) is a chronic inflammation of the large and/or small intestines which generally occurs in young adults. In 65% of CD sufferers, the large intestine is inflamed, while 35% of people suffering from the disease have inflammation in the small intestine. In CD, the inflammation occurs in all layers of the small or large intestine as well as nearby tissues and lymph nodes. Areas of inflamed tissue are often separated by areas of normal tissue, however. The sores and swollen areas of the intestine may thicken and eventually block the intestines. This inflammation can also cause holes and sores in the bowel walls. Because the inflammation also affects the outer intestinal walls, the loops of the bowel may attach to each other, as well.

Symptoms of CD include: abdominal pain or cramping, diarrhea, fever, weight loss, rectal fistulas (i.e. abnormal opening at or near the anus), and rectal fissures.

The present invention is directed to a method of treating Crohn's Disease, and in particular comprises the oral administration of a therapeutically effective amount of limonene, preferably a purified form of d-limonene, to a person in need of such treatment.

DESCRIPTION OF THE PREFERRED EMBODIMENTS:

The present invention is directed to a method for treating CD and comprises the oral administration of a therapeutically effective amount of limonene, preferably a purified form of d-limonene (i.e. at least 98%), to a person in need of such treatment. "Limonene" as used herein shall include both d-limonene and 1-limonene.

The therapeutic regimen for treating CD, as defined further below, comprises the oral administration of a therapeutically effective amount of limonene, wherein the limonene is administered once a day for a time sufficient to alleviate or eliminate entirely the severity and frequency of the CD symptoms, such symptoms including abdominal pain or cramping, diarrhea, fever, weight loss, rectal fistulas, and/or rectal fissures, sometimes accompanied by anal bleeding. As used herein, "treatment" shall mean temporary or permanent alleviation or elimination of CD symptoms and/or intestinal damage.

A preferred adult dose of limonene is about 400 to 1,000 milligrams, more preferably 1,000 mg, administered once daily, typically for a period of 10 to 30 days. Other dosing regimens, such as every other day and twice weekly regimens, may be desired, depending upon the patient. In fact, it will be appreciated by those of ordinary skill in the art that the amount of limonene, dosing schedule, and duration of treatment may vary depending upon the individual's age, weight, and severity of the CD.

A preferred pharmaceutical formulation is a gelatin capsule, including soft-gel capsules, although the limonene may be formulated in suspension, emulsion, or solution. Alternatively, the limonene may be orally administered as the natural oil.

A preferred formulation of limonene comprises a highly purified form of limonene, preferably 98–99% purity. Any conventional distillation method known by those of ordinary skill in the art for obtaining a highly purified form of d-limonene may be employed. Example 1 below illustrates one preferred distillation method for removing the majority of contaminants.

The foregoing treatment regimens were conducted on two patients suffering from CD, as described in more detail in Examples 2 and 3, below, with excellent results.

EXAMPLE 1

An atmospheric distillation unit was charged with 100 milliliters of 96–96.5% Food Grade limonene. The distillation unit was operated with a reflux ratio of 1:1. The desired limonene distillate was removed in a range of from about 340° F. to 390° F. and was of a purity of about 98%.

EXAMPLE 2

A 48-year old male subject, diagnosed with CD at the age of 22 (diagnosis confirmed by colonoscopy), exhibited severe abdominal pain, an average often stools/day, and anal bleeding for six years prior to treatment with the inventive method. Upon diagnosis, the patient underwent a partial small bowel surgical resection wherein about one foot of intestine and appendix were surgically removed.

To alleviate the symptoms of CD, the subject was taking the following prescriptions and over-the-counter medications: 1 Cortisone injection every six months; 1 tablet of 2.5 mg diphenoxylate/0.025 mg atropine every 8 hours as needed; twelve tablets (2.0 mg each) of IMODIUM (loperamide) every day as needed.

Prior to treatment with the limonene regimen, the subject discontinued taking his prescription and OTC medications for CD except for one cortisone injection in April 2001 and about 1 to 2 tablets of IMODIUM (lopcramide) per month. He began taking 1000 mg d-limonene (98%) on March 2001. The subject developed severe acid reflux, and discontinued the regimen immediately. The subject then began taking 400 mg of d-limonene once a week for two weeks, followed by 400-mg d-limonene twice a week for three weeks. The subject was then put on a regimen of 1000 mg d-limonene take once a week for three weeks, increasing to 1000 mg twice a week for three weeks. After that series, the subject began taking 1000 mg d-limonene every other day for three weeks. The subject continued to take 1000 mg d-limonene twice a week for maintenance. During treatment with d-limonene, anal bleeding stopped almost immediately when taking 1000 mg. During maintenance, the subject began having normal stools 1 to 2 times a day with no abdominal pain or cramping.

EXAMPLE 3

A 45-year old male subject diagnosed with CD in November 1999 after undergoing a colonoscopy. His symptoms included severe abdominal pain and pressure, an average of ten stools/day, and anal bleeding. After undergoing a medication regimen of six tablets of ASACOL (mesalamine) daily and two 50 mg tablets of IMURAN (azathioprine) daily, his bleeding ceased for about six to eight months, and then reoccurred.

The subject began treatment with the inventive limonene method in January 2001, taking 1000 mg of d-limonene daily. About seven days alter treatment, the subject experienced a normal 1–2 stools per day with no anal bleeding. For maintenance therapy, the patient continued to take three 1000 mg capsules of d-limonene per week.

I claim:

1. A method for treating Crohn's Diseases, said method comprising orally administering to a person in need of such treatment a therapeutically effective amount of limonene, wherein the administered amount of said limonene has a purity of at least 98%.

2. The method of claim 1, wherein mid amount of limonene is from 400 mg to 1000 mg administered every day to said person.

3. The method of claim 2, wherein said amount of limonene is administered for a period of 10 to 30 days.

4. The method of claim 1, wherein said amount of limonene is from 400 mg to 1000 mg administered every other day to said person.

5. The method of claim 4, wherein said amount of limonene is administered for a period of 10 to 30 days.

6. The method of claim 1, wherein said amount of limonene is from 400 mg to 1000 mg administered twice a week to said person.

* * * * *

UNITED STATES PATENT AND TRADEMARK OFFICE
CERTIFICATE OF CORRECTION

| | | |
|---|---|---|
| PATENT NO. | : 7,041,706 B2 | Page 1 of 1 |
| APPLICATION NO. | : 10/419572 | |
| DATED | : May 9, 2006 | |
| INVENTOR(S) | : Joe S. Wilkins, Jr. | |

It is certified that error appears in the above-identified patent and that said Letters Patent is hereby corrected as shown below:

On col. 2, line 24, replace the term "often" with the terms -- of ten --

Signed and Sealed this

Fifteenth Day of August, 2006

JON W. DUDAS
*Director of the United States Patent and Trademark Office*